United States Patent
Harel

(10) Patent No.: US 10,524,133 B2
(45) Date of Patent: Dec. 31, 2019

(54) RADIO FREQUENCY (RF) COMMUNICATION CHANNEL RECONFIGURATION IN REMOTE ANTENNA UNIT (RAU) COVERAGE AREAS IN A DISTRIBUTED ANTENNA SYSTEM (DAS) TO REDUCE RF INTERFERENCE

(71) Applicant: Corning Optical Communications Wireless Ltd, Airport City (IL)

(72) Inventor: Dror Harel, Hod Hasharon (IL)

(73) Assignee: Corning Optical Communications LLC, Charlotte, NC (US)

( * ) Notice: Subject to any disclaimer, the term of this patent is extended or adjusted under 35 U.S.C. 154(b) by 0 days.

(21) Appl. No.: 15/807,286

(22) Filed: Nov. 8, 2017

(65) Prior Publication Data
US 2018/0070241 A1  Mar. 8, 2018

Related U.S. Application Data

(63) Continuation of application No. PCT/IL2016/050586, filed on Jun. 7, 2016.
(Continued)

(51) Int. Cl.
*H04W 16/10* (2009.01)
*H04W 88/08* (2009.01)

(52) U.S. Cl.
CPC .......... *H04W 16/10* (2013.01); *H04W 88/085* (2013.01)

(58) Field of Classification Search
CPC .... H04W 16/10; H04W 88/085; A61B 5/024; A61B 5/02055; A61B 5/0816; A61B 5/14542; A61B 5/022; A61B 2560/046
See application file for complete search history.

(56) References Cited

U.S. PATENT DOCUMENTS 4,334,322 A   6/1982  Clark, III
7,286,507 B1 * 10/2007  Oh ........................ H04W 16/26
                                                  370/312
(Continued)

OTHER PUBLICATIONS

Iinternational Search Report and Written Opinion of the International Searching Authority; PCT/IL2016/050586; dated Sep. 19, 2016; 11 pages; European Patent Office.

*Primary Examiner* — Dady Chery
(74) *Attorney, Agent, or Firm* — C. Keith Montgomery

(57) ABSTRACT

One embodiment of the disclosure relates to radio frequency (RF) communication channel reconfiguration in remote antenna unit (RAU) coverage areas in a distributed antenna system (DAS) to reduce RF interferences. In this regard, a spectrum optimization unit dynamically reconfigures RF communication channels employed by RAU coverage areas in a DAS to reduce or avoid adjacent-channel and/or co-channel RF interferences. Each of the RAU coverage areas provides a respective sniffed RF signal to the spectrum optimization unit. The spectrum optimization unit analyzes the respective sniffed RF signal to determine a respective lesser-interfered RF communication channel for an RAU coverage area and dynamically reconfigures the RAU coverage area to communicate on the respective lesser-interfered RF communication channel. By dynamically reconfiguring the RAU coverage areas to communicate on respective lesser-interfered RF communication channels, it is possible to reduce or avoid RF interferences to provide improved capacity, throughput, and coverage in the DAS.

21 Claims, 8 Drawing Sheets

Related U.S. Application Data

(60) Provisional application No. 62/173,167, filed on Jun. 9, 2015.

(56) References Cited

U.S. PATENT DOCUMENTS

| | | |
|---|---|---|
| 9,693,321 B2 | 6/2017 | Venkatraman et al. |
| 2003/0035388 A1* | 2/2003 | Schmidt ................. H04L 63/04 370/329 |
| 2004/0218563 A1 | 11/2004 | Porter et al. |
| 2005/0073979 A1* | 4/2005 | Barber ................ H04L 12/2856 370/338 |
| 2011/0105184 A1* | 5/2011 | Piirainen ................ H04B 7/022 455/562.1 |
| 2012/0039320 A1* | 2/2012 | Lemson ................ H03F 1/3247 370/338 |
| 2013/0295980 A1 | 11/2013 | Reuven et al. |
| 2014/0024402 A1 | 1/2014 | Singh |

\* cited by examiner

RADIO FREQUENCY (RF) COMMUNICATION CHANNEL RECONFIGURATION IN REMOTE ANTENNA UNIT (RAU) COVERAGE AREAS IN A DISTRIBUTED ANTENNA SYSTEM (DAS) TO REDUCE RF INTERFERENCE

PRIORITY APPLICATIONS

This is a continuation of International App. No. PCT/IL2016/050586, filed Jun. 7, 2016, which claims the benefit of priority under 35 U.S.C. § 119 of U.S. Provisional Application No. 62/173,167 filed on Jun. 9, 2015, the content of which is relied upon and incorporated herein by reference in its entirety.

BACKGROUND

The disclosure relates generally to distribution of communications signals in a distributed antenna system (DAS), and more particularly to radio frequency (RF) communication channel reconfiguration in remote antenna unit (RAU) coverage areas to reduce RF interferences.

Wireless customers are increasingly demanding digital data services, such as streaming video signals. Some wireless customers use their wireless devices in areas that are poorly serviced by conventional cellular networks, such as inside certain buildings or areas where there is less cellular coverage. One response to the intersection of these two concerns has been the use of DASs. The DASs can be particularly useful when deployed inside buildings or other indoor environments where client devices may not otherwise be able to effectively receive RF signals from a source. The DASs are configured to provide multiple coverage areas inside the buildings to support higher capacity and better RF coverage. Each coverage area includes one or more RAUs configured to receive and transmit communications signals to the client devices within antenna range of the RAU(s).

The RAUs located in the multiple DAS coverage areas may be configured to provide a variety of wireless services, such as wideband code division multiple access (WCDMA), long term evolution (LTE), and wireless local area network (WLAN) and Wireless Fidelity (Wi-Fi) communications services, as examples. In some cases, the RF signals associated with the variety of wireless services may be transmitted and/or received on adjacent or overlapping RF channels. This can cause adjacent-channel or co-channel RF interferences between the RAUs located in the multiple DAS coverage areas. For example, the adjacent-channel RF interferences can occur between one RAU configured to provide WLAN services on channel one (1) of a 2.4 GigaHertz (GHz) band (2.402 GHz-2.422 GHz) and another RAU configured to provide LTE services on an LTE band (2.3 GHz-2.4 GHz). For example, maximum transmission powers of LTE RF signals and WLAN signals may be 60 decibel-millwatts (dBm) and 30 dBm, respectively. As a result, capacity, throughput, and coverage of the WLAN services can be severely degraded by the higher-powered LTE RF signals.

It may be possible to map out all RF bands and/or channels among the multiple DAS coverage areas during initial deployment of the DASs to avoid the adjacent-channel and the co-channel RF interferences in the DAS. However, it is difficult to anticipate every communications service and every RF spectrum distributed by the DAS during the initial deployment, since new communications services, new RF spectrums, new coverage areas, and/or new RAUs may be added to the DAS at a later time.

No admission is made that any reference cited herein constitutes prior art. Applicant expressly reserves the right to challenge the accuracy and pertinency of any cited documents.

SUMMARY

One embodiment of the disclosure relates to radio frequency (RF) communication channel reconfiguration in remote antenna unit (RAU) coverage areas in a distributed antenna system (DAS) to reduce RF interferences. In DASs disclosed herein, a plurality of RAU coverage areas is provided in the DAS. Each RAU coverage area can be configured to provide wireless communications services on a set of RF bands. However, the set of RF bands may be susceptible to RF performance degradations resulting from RF interferences produced by RF transmitters (e.g., a cellular base station) located outside the RAU coverage area. In this regard, to reduce the RF interferences in the RAU coverage area, a spectrum optimization unit is provided. The spectrum optimization unit can be provided in a head-end equipment (HEE) of the DAS as an example. The spectrum optimization unit is configured to dynamically reconfigure RF communication channels employed by RAUs in the RAU coverage area to reduce or avoid adjacent-channel and/or co-channel RF interferences. At least one of the RAUs in the RAU coverage area is configured to sniff RF signals, which may include the RF interferences produced by the RF transmitters located outside the RAU coverage area, and provide the sniffed RF signals to the spectrum optimization unit. The spectrum optimization unit analyzes the sniffed RF signals to determine a lesser-interfered RF communication channel for the RAUs in the RAU coverage area. The spectrum optimization unit is further configured to dynamically reconfigure the RAUs in the RAU coverage area to communicate on the lesser-interfered RF communication channel. By dynamically determining and reconfiguring the RAUs in the RAU coverage area to communicate on the lesser-interfered RF communication channel, it is possible to reduce or avoid the adjacent-channel and the co-channel RF interferences to provide improved capacity, throughput, and coverage in the RAU coverage area.

One embodiment of the disclosure relates to a spectrum optimization unit in a DAS. The spectrum optimization unit comprises a spectrum analysis unit communicatively coupled to a plurality of RAU coverage areas in a DAS, the plurality of RAU coverage areas each configured to communicate on a respective first RF channel. The spectrum analysis unit is configured to receive a plurality of sniffed RF signals from the plurality of RAU coverage areas, respectively, wherein each of the plurality of sniffed RF signals comprises one or more RF signals sniffed by at least one RAU in a respective RAU coverage area. For each of the plurality of sniffed RF signals, the spectrum analysis unit is configured to analyze the one or more RF signals comprised in the sniffed RF signals. For each of the plurality of sniffed RF signals, the spectrum analysis unit is also configured to determine a respective second RF channel for the respective RAU coverage area if the respective second RF channel is lesser-interfered than the respective first RF channel. The spectrum optimization unit also comprises a controller configured to reconfigure one or more RAU coverage areas among the plurality of RAU coverage areas to communicate on one or more respective second RF channels in response to the one or more respective second RF channels being determined by the spectrum analysis unit.

Another embodiment of the disclosure relates to a method for reducing RF interferences in a plurality of RAU coverage areas in a DAS. The method comprises receiving a plurality of sniffed RF signals from a plurality of RAU coverage areas, respectively. Each of the plurality of RAU coverage areas is configured to communicate on a respective first RF channel. For each of the plurality of sniffed RF signals received from the plurality of RAU coverage areas, the method also comprises analyzing the plurality of sniffed RF signals to determine a respective second RF channel for a respective RAU coverage area if the respective second RF channel is lesser-interfered than the respective first RF channel of the respective RAU coverage area. For each of the plurality of sniffed RF signals received from the plurality of RAU coverage areas, the method also comprises reconfiguring the respective RAU coverage area to communicate on the respective second RF channel.

Another embodiment of the disclosure relates to a DAS. The DAS comprises a plurality of RAU coverage areas in a DAS. Each of the plurality of RAU coverage areas is configured to communicate on a respective first RF channel. The DAS also comprises an HEE coupled to the plurality of RAU coverage areas over a plurality of communications mediums, respectively. The HEE comprises a spectrum optimization unit. The spectrum optimization unit comprises a spectrum analysis unit. The spectrum analysis unit is configured to receive a plurality of sniffed RF signals from the plurality of RAU coverage areas, respectively. Each of the plurality of sniffed RF signals comprises one or more RF signals sniffed by at least one RAU in a respective RAU coverage area. For each of the plurality of sniffed RF signals, the spectrum analysis unit is configured to analyze the one or more RF signals comprised in the plurality of sniffed RF signals. For each of the plurality of sniffed RF signals, the spectrum analysis unit is also configured to determine a respective second RF channel for the respective RAU coverage area if the respective second RF channel is lesser-interfered than the respective first RF channel. The spectrum optimization unit also comprises a controller configured to reconfigure one or more RAU coverage areas among the plurality of RAU coverage areas to communicate on one or more respective second RF channels in response to the one or more respective second RF channels being determined by the spectrum analysis unit.

Additional features and advantages will be set forth in the detailed description which follows, and in part will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding, and are incorporated in and constitute a part of this specification. The drawings illustrate one or more embodiments and, together with the description, serve to explain principles and operation of the various embodiments.

DETAILED DESCRIPTION

One embodiment of the disclosure relates to radio frequency (RF) communication channel reconfiguration in remote antenna unit (RAU) coverage areas in a distributed antenna system (DAS) to reduce RF interferences. In DASs disclosed herein, a plurality of RAU coverage areas is provided in the DAS. Each RAU coverage area can be configured to provide wireless communications services on a set of RF bands. However, the set of RF bands may be susceptible to RF performance degradations resulting from RF interferences produced by RF transmitters (e.g., a cellular base station) located outside the RAU coverage area. In this regard, to reduce the RF interferences in the RAU coverage area, a spectrum optimization unit is provided. The spectrum optimization unit can be provided in a head-end equipment (HEE) of the DAS as an example. The spectrum optimization unit is configured to dynamically reconfigure RF communication channels employed by RAUs in the RAU coverage area to reduce or avoid adjacent-channel and/or co-channel RF interferences. At least one of the RAUs in the RAU coverage area is configured to sniff RF signals, which may include the RF interferences produced by the RF transmitters located outside the RAU coverage area, and provide the sniffed RF signals to the spectrum optimization unit. The spectrum optimization unit analyzes the sniffed RF signals to determine a lesser-interfered RF communication channel for the RAUs in the RAU coverage area. The spectrum optimization unit is further configured to dynamically reconfigure the RAUs in the RAU coverage area to communicate on the lesser-interfered RF communication channel. By dynamically determining and reconfiguring the RAUs in the RAU coverage area to communicate on the lesser-interfered RF communication channels, it is possible to reduce or avoid the adjacent-channel and the co-channel RF interferences to provide improved capacity, throughput, and coverage in the RAU coverage area.

Figure 1:
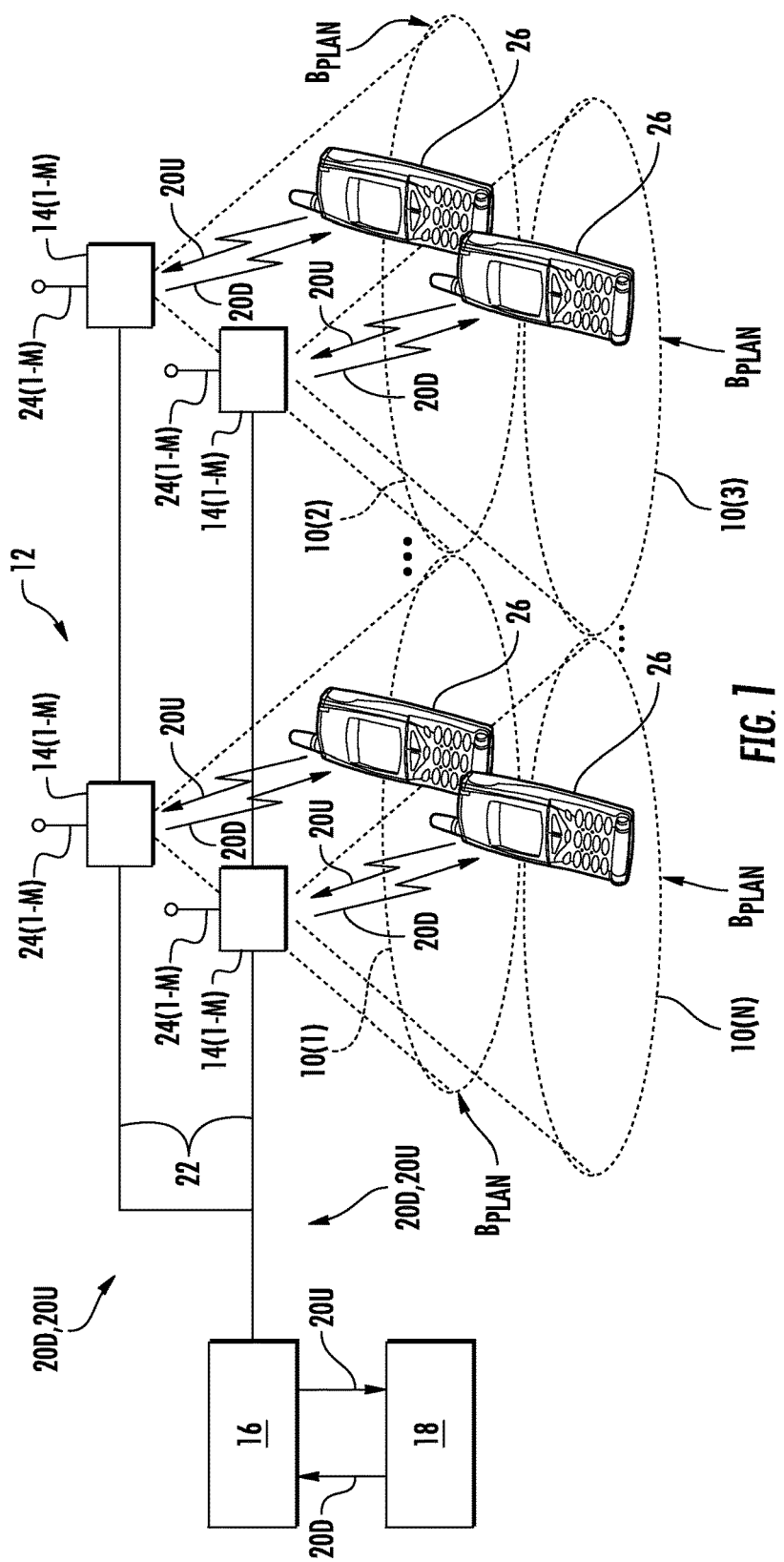
FIG. 1 is a schematic diagram of an exemplary distributed antenna system (DAS)
Figure 2B:
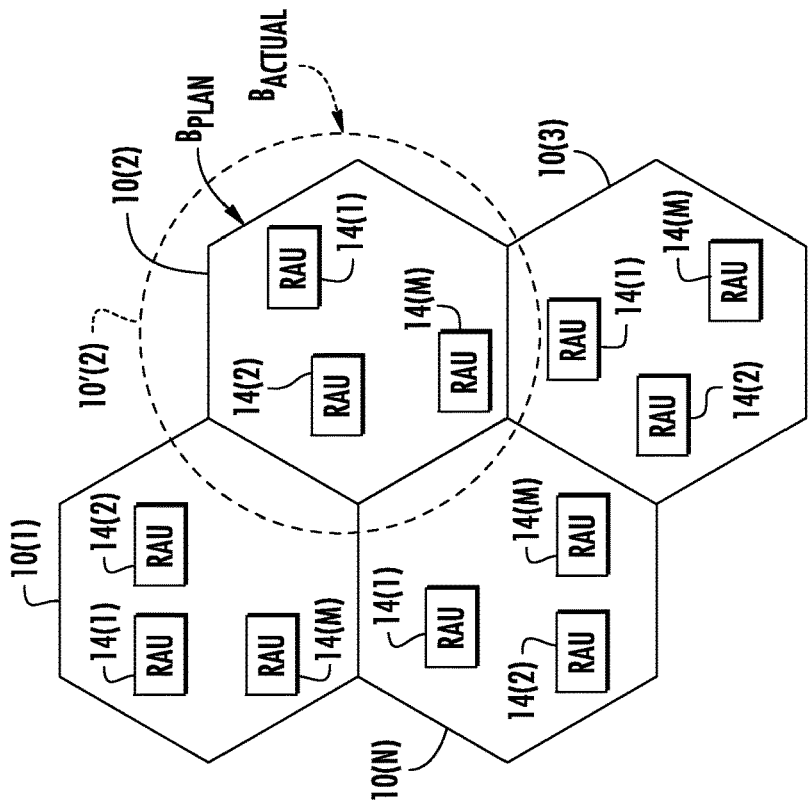
FIG. 2B is an exemplary illustration of an over-sized RAU coverage area with an expanded coverage boundary that is larger than a planned coverage boundary.
Figure 2A:
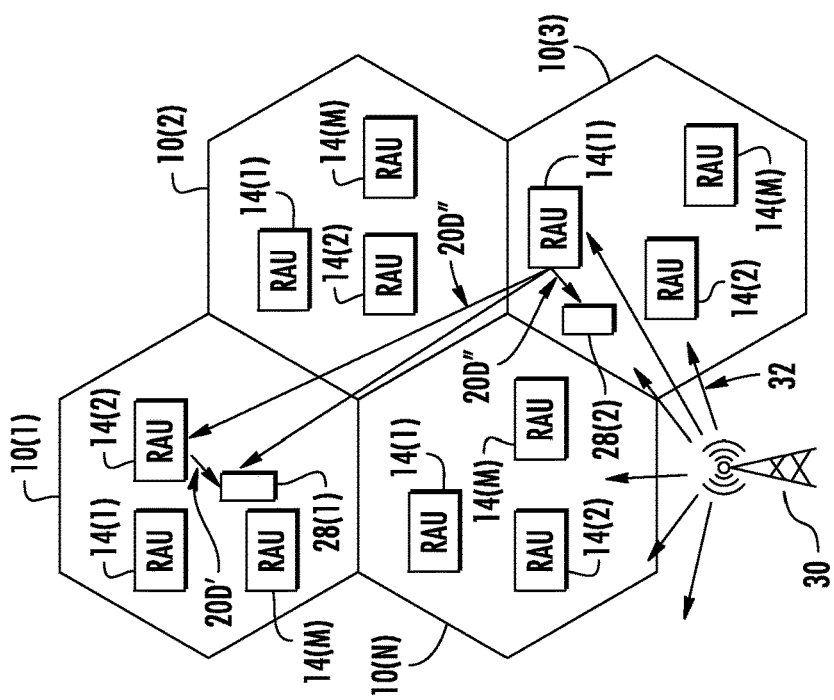
FIG. 2A is an exemplary illustration of adjacent-channel and co-channel RF interferences that may occur among remote antenna unit (RAU) coverage areas in the DAS of FIG. 1.
Figure 3:
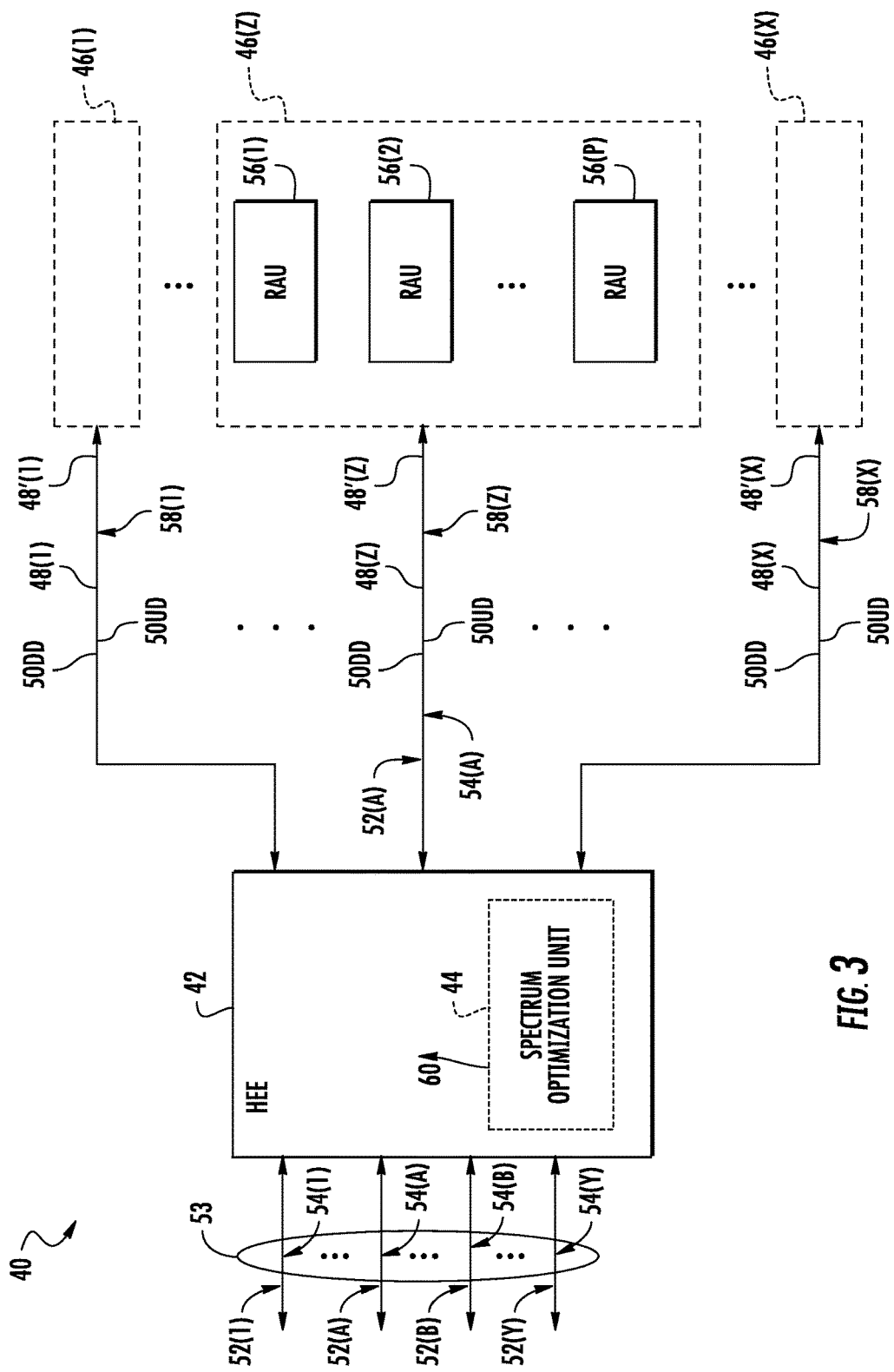
FIG. 3 is a schematic diagram of an exemplary DAS, wherein a head-end equipment (HEE) comprises a spectrum optimization unit configured to detect and reduce the adjacent-channel and the co-channel RF interferences among a plurality of RAU coverage areas.

Before discussing examples of RF communication channel reconfiguration in RAU coverage areas in a DAS to reduce RF interferences starting at FIG. 3, discussion of an exemplary DAS that employs a communications medium to support wireless communications services to a plurality of RAUs as well as RF interference scenarios between the plurality of RAUs are first provided with references to FIGS. 1, 2A, and 2B. The discussion of specific exemplary aspects of RF communication channel reconfiguration in the RAU coverage areas in the DAS to reduce the RF interferences starts later with reference to FIG. 3.

In this regard, FIG. 1 illustrates a distribution of communications services to RAU coverage areas 10(1)-10(N) of a DAS 12, wherein 'N' is the number of RAU coverage areas. These communications services can include cellular services such as long-term evolution (LTE), wireless services such as Wireless Fidelity (Wi-Fi) and BLUETOOTH™, and combinations thereof, as examples. The RAU coverage areas 10(1)-10(N) may be remotely located. Each of the RAU coverage areas 10(1)-10(N) is created by and centered on one or more RAUs 14(1-M) connected to an HEE 16 (e.g., a head-end controller or head-end unit or central unit), wherein M may represent different finite positive integers in the RAU coverage areas 10(1)-10(N). Each of the RAU coverage areas 10(1)-10(N) corresponds to a planned coverage boundary BPLAN. The HEE 16 may be communicatively coupled to a signal source 18, for example, a base transceiver station (BTS) or a baseband unit (BBU). In this regard, the HEE 16 receives downlink communications signals 20D, which may comprise downlink communications signals from a variety of communications services, from the signal source 18 to be distributed to the one or more RAUs 14(1-M) in each of the RAU coverage areas 10(1)-10(N). Each of the one or more RAUs 14(1-M) is configured to receive the downlink communications signals 20D from the HEE 16 over a communications medium 22 to be distributed to the respective RAU coverage areas 10(1)-10(N) of the one or more RAUs 14(1-M). In a non-limiting example, the communications medium 22 may be a wired communications medium, a wireless communications medium, or an optical fiber-based communications medium. Each of the one or more RAUs 14(1-M) in each of the RAU coverage areas 10(1)-10(N) may include an RF transmitter/receiver (not shown) and a respective antenna 24(1-M) operably connected to the RF transmitter/receiver to wirelessly distribute the communications services to client devices 26 within the respective RAU coverage areas 10(1)-10(N). The one or more RAUs 14(1-M) are also configured to receive uplink communications signals 20U, which may comprise uplink communications signals corresponding to the variety of communications services, from the client devices 26 within the respective RAU coverage areas 10(1)-10(N) to be distributed to the signal source 18. The size of each of the RAU coverage areas 10(1)-10(N) is determined by amount of RF power transmitted by the one or more respective RAUs 14(1-M), receiver sensitivity, antenna gain, and RF environment, as well as by RF transmitter/receiver sensitivity of the client devices 26. The client devices 26 usually have a fixed maximum RF receiver sensitivity so that the above-mentioned properties of the one or more RAUs 14(1-M) mainly determine the size of each of the respective RAU coverage areas 10(1)-10(N).

With continuing reference to FIG. 1, the downlink communications signals 20D and the uplink communications signals 20U may be distributed by the RAU coverage areas 10(1)-10(N) on adjacent or overlapping downlink and uplink RF communication channels (not shown). As a result, adjacent-channel or co-channel RF interference can occur among the RAU coverage areas 10(1)-10(N). In this regard, FIG. 2A is an exemplary illustration of the adjacent-channel and the co-channel RF interferences that may occur in the RAU coverage areas 10(1)-10(N) of FIG. 1. Common elements between FIGS. 1 and 2A are shown therein with common element numbers and will not be re-described herein.

With reference to FIG. 2A, in RAU coverage area 10(1) for example, RAU 14(1) transmits a downlink communications signal 20D' to a client device 28(1) on Wi-Fi channel one (1) that ranges from 2.402 Gigahertz (GHz) to 2.422 GHz (not shown). The RAU 14(1) in RAU coverage area 10(3) is also transmitting a downlink communications signal 20D" to a client device 28(2) on the Wi-Fi channel 1. The RAU 14(1) in the RAU coverage area 10(3) may be transmitting the downlink communications signal 20D" at a higher power, which causes the downlink communications signal 20D" to leak into the RAU coverage area 10(1). As a result, an RF receiver (not shown) of the client device 28(1) may be blocked by the leaked downlink communications signal 20D" and unable to receive the downlink communications signal 20D' correctly.

With continuing reference to FIG. 2A, in a non-limiting example, a BTS 30, which may be located inside or outside the RAU coverage area 10(3), transmits a downlink communications signal 32 on LTE band forty (40) that ranges from 2.3 GHz to 2.4 GHz. In this regard, there are only two (2) Megahertz (MHz) of RF separation between the upper boundary (i.e., 2.4 GHz) of the LTE band 40 and the lower boundary (i.e., 2.402 GHz) of the Wi-Fi channel 1. Because the BTS 30 is configured to transmit the downlink communications signal 32 at a higher RF power, an RF receiver (not shown) of the client device 28(2) may lose receiving sensitivity and be unable to receive the downlink communications signal 20D" from the RAU 14(1) in the RAU coverage area 10(3) correctly.

With reference back to FIG. 1, when the DAS 12 is deployed, each of the RAU coverage areas 10(1)-10(N) is configured with the planned coverage boundary BPLAN to provide a planned capacity. In a non-limiting example, the planned capacity may be determined based on software simulations. However, the one or more RAUs 14(1-M) in one of the RAU coverage areas 10(1)-10(N), for example, RAU coverage area 10(2), may be transmitting at a higher RF power. As a result, the RAU coverage area 10(2), for example, may become an over-sized RAU coverage area and thus reducing the planned capacity of the RAU coverage area 10(2). In this regard, FIG. 2B is an exemplary illustration of an over-sized RAU coverage area 10'(2) with an expanded coverage boundary $B_{ACTUAL}$ that is larger than the planned coverage boundary BPLAN. Common elements between FIGS. 1 and 2B are shown therein with common element numbers and will not be re-described herein.

As shown in FIG. 2B, the expanded coverage boundary $B_{ACTUAL}$ of the RAU coverage area 10(2) is larger than the planned coverage boundary BPLAN because the one or more RAUs 14(1-M) may be transmitting at a higher power level. As a result of the expanded coverage boundary $B_{ACTUAL}$, the planned capacity of the RAU coverage area 10(2) may be reduced.

The adjacent-channel and the co-channel RF interference scenarios discussed above in reference to FIG. 2A can have severe impact on capacities, throughputs, and coverage ranges of the RAU coverage areas 10(1)-10(N). Hence, it is desirable to dynamically detect and reduce the adjacent-channel and the co-channel RF interferences in the RAU coverage areas 10(1)-10(N). In this regard, as will be discussed in more detail below, FIG. 3 is a schematic diagram of an exemplary DAS 40, wherein an HEE 42 comprises a spectrum optimization unit 44 configured to detect and reduce the adjacent-channel and the co-channel RF interferences in a plurality of RAU coverage areas 46(1)-46(X).

With reference to FIG. 3, the HEE 42 is communicatively coupled to the plurality of RAU coverage areas 46(1)-46(X) by a plurality of communications mediums 48(1)-48(X). In a non-limiting example, each of the plurality of communications mediums 48(1)-48(X) comprises a respective downlink data signal path 50DD and a respective uplink data signal path 50UD. In another non-limiting example, the plurality of communications mediums 48(1)-48(X) may be a plurality of optical fiber-based communications mediums 48'(1)-48'(X). In another non-limiting example, in the plurality of optical fiber-based communications mediums 48'(1)-48'(X), the respective downlink data signal path 50DD is provided by a respective downlink data optical fiber (not shown) and the respective uplink data signal path 50UD is provided by a respective uplink data optical fiber (not shown).

With continuing reference to FIG. 3, the HEE 42 receives one or more downlink communications signals 52(1)-52(Y) from one or more communications signal sources (not shown). The one or more downlink communications signals 52(1)-52(Y) correspond to an RF channel set 53 that may comprise multiple downlink RF channels (not shown). In other words, each of the one or more downlink communications signals 52(1)-52(Y) determines a downlink RF channel to be used for communicating a respective downlink communications signal. The one or more downlink communications signals 52(1)-52(Y) are provided to the plurality of RAU coverage areas 46(1)-46(X) over the respective downlink data signal path 50DD in the plurality of communications mediums 48(1)-48(X). In this regard, each of the plurality of RAU coverage areas 46(1)-46(X) is configured to operate on the downlink RF channel determined by the downlink communications signal being provided to the respective RAU coverage area. The HEE 42 also provides one or more uplink communications signals 54(1)-54(Y) to the one or more communications signal sources, respectively. The one or more uplink communications signals 54(1)-54(Y) are received from the plurality of RAU coverage areas 46(1)-46(X) over the respective uplink data signal path 50UD in the plurality of communications mediums 48(1)-48(X). For convenience of discussion and illustration, RAU coverage area 46(Z), which may be any of the plurality of RAU coverage areas 46(1)-46(X), is discussed hereinafter as a non-limiting example.

With continuing reference to FIG. 3, the RAU coverage area 46(Z) comprises a plurality of RAUs 56(1)-56(P). The RAU coverage area 46(Z) is configured to receive downlink communications signal 52(A) from the HEE 42 and provides uplink communications signal 54(A) to the HEE 42. Each of the plurality of RAUs 56(1)-56(P) is configured to communicate with one or more client devices (not shown) on a first RF channel (not shown) determined by the downlink communications signal 52(A). As previously shown in FIG. 2A, the RAU coverage area 46(Z) may experience interference from the downlink communications signal 20D" and/or the downlink communications signal 32. In this regard, at least one RAU among the plurality of RAUs 56(1)-56(P) in the RAU coverage area 46(Z) is configured to generate a sniffed RF signal 58(Z). In a non-limiting example, the sniffed RF signal 58(Z) may be a sniffed downlink RF signal. In another non-limiting example, the sniffed RF signal 58(Z) may be a sniffed uplink RF signal. In this regard, in the DAS 40, the plurality of RAU coverage areas 46(1)-46(X) may provide a plurality of sniffed RF signals 58(1)-58(X) to the spectrum optimization unit 44, respectively. The sniffed RF signal 58(Z) may include one or more downlink RF signals, including the downlink communications signal 20D" and/or the downlink communications signal 32, that are present in the RAU coverage area 46(Z) and can be sniffed by at least one RAU among the plurality of RAUs 56(1)-56(P). The sniffed RF signal 58(Z) may also include one or more uplink RF signals in the first RF channel. The sniffed RF signal 58(Z) may also include one or more configured RF signals (e.g., RF signals communicated by Wi-Fi access points) in the first RF channel. The sniffed RF signal 58(Z) may also include one or more ad hoc RF signals (e.g., RF signals emitted by microwave oven) in the first RF channel. In a non-limiting example, the sniffed RF signal 58(Z) may be provided to the HEE 42 as an in-band control signal over the respective uplink data signal path 50UD in communications medium 48(Z).

With continuing reference to FIG. 3, the HEE 42 includes the spectrum optimization unit 44 to detect and reduce the adjacent-channel and the co-channel RF interferences in the RAU coverage area 46(Z). In this regard, the spectrum optimization unit 44 in the HEE 42 in this example receives and analyzes the sniffed RF signal 58(Z) provided by the RAU coverage area 46(Z). By analyzing the sniffed RF signal 58(Z), the spectrum optimization unit 44 can determine whether there exists a second RF channel (not shown) in the RF channel set 53 that is lesser-interfered than the first RF channel used by the RAU coverage area 46(Z). The spectrum optimization unit 44 may determine the second RF channel that is lesser-interfered than the first RF channel based on a range of factors, including but not limited to signal-to-noise ratio (SNR), received-signal-strength indication (RSSI), bit error rate (BER), and strength of the sniffed RF signal 58(Z). The spectrum optimization unit 44 may reference the range of factors individually or in combination to determine the second RF channel that is lesser-interfered than the first RF channel. In one non-limiting example, the second RF channel may be different from the first RF channel, indicating that the second RF channel is lesser-interfered than the first RF channel. In another non-limiting example, the second RF channel may be the same as the first RF channel, indicating that the second RF channel does not exist. In this regard, if the second RF channel exists for the RAU coverage area 46(Z), the spectrum optimization unit 44 can reconfigure the RAU coverage area 46(Z) to communicate on the second RF channel, thus reducing the adjacent-channel and/or the co-channel interferences in the RAU coverage area 46(Z). To do so, the spectrum optimization unit 44 may reroute downlink communications signal 52(B), which is associated with the second RF channel as an example, to the RAU coverage area 46(Z). In a non-limiting example, the spectrum optimization unit 44 may continue routing the downlink communications signal 52(A), which is associated with the first RF channel, to the RAU coverage area 46(Z) or rerouting the downlink communications signal 52(A) to another RAU coverage area among the plurality of RAU coverage areas 46(1)-46(X). In another non-limiting example, the spectrum optimization unit 44 may reroute the downlink communications signal 52(A) and the downlink communications signal 52(B) via a channel control signal 60. In another non-limiting example, the spectrum optimization unit 44 may also analyze the sniffed RF signal 58(Z) to determine a downlink RF signal among the one or more downlink RF signals and the one or more uplink RF signals comprised in the sniffed RF signal 58(Z) received from a cellular base station (BS) or a mobile station (MS).

With continuing reference to FIG. 3, the spectrum optimization unit 44 also analyzes the sniffed RF signal 58(Z) to detect a power-leaking RAU that interferes with the RAU coverage area 46(Z) from another RAU coverage area that is different from the RAU coverage area 46(Z). If there exists the power-leaking RAU, the spectrum optimization unit 44 can reduce RF power level of the power-leaking RAU, thus reducing the adjacent-channel or the co-channel interference caused by the power-leaking RAU in the RAU coverage area 46(Z). In a non-limiting example, the RF power level of the power-leaking RAU may be reduced manually or via a power control signal (not shown) provided by the spectrum optimization unit 44.

Furthermore, by analyzing the sniffed RF signal 58(Z), the spectrum optimization unit 44 is also able to determine whether the RAU coverage area 46(Z) is an over-sized RAU coverage area with an expanded coverage boundary $B_{ACTUAL}$, such as the over-sized RAU coverage area 10'(2) of FIG. 2B. Accordingly, the spectrum optimization unit 44 can reduce RF power levels of one or more RAUs among the plurality of RAUs 56(1)-56(P) in the RAU coverage area 46(Z) to reduce coverage boundary of the RAU coverage area 46(Z), thus ensuring sufficient capacity in the RAU coverage area 46(Z).

Hence, by dynamically reconfiguring the RAU coverage area 46(Z) to communicate on the second RF channel, it is possible to reduce or avoid the adjacent-channel and the co-channel RF interferences in the RAU coverage area 46(Z) to provide improved capacity, throughput, and coverage in the RAU coverage area 46(Z). Accordingly, by reducing the adjacent-channel and the co-channel RF interferences in each of the plurality of RAU coverage areas 46(1)-46(X), it is possible to reduce or avoid the adjacent-channel and the co-channel RF interferences in the DAS 40.

Figure 4:
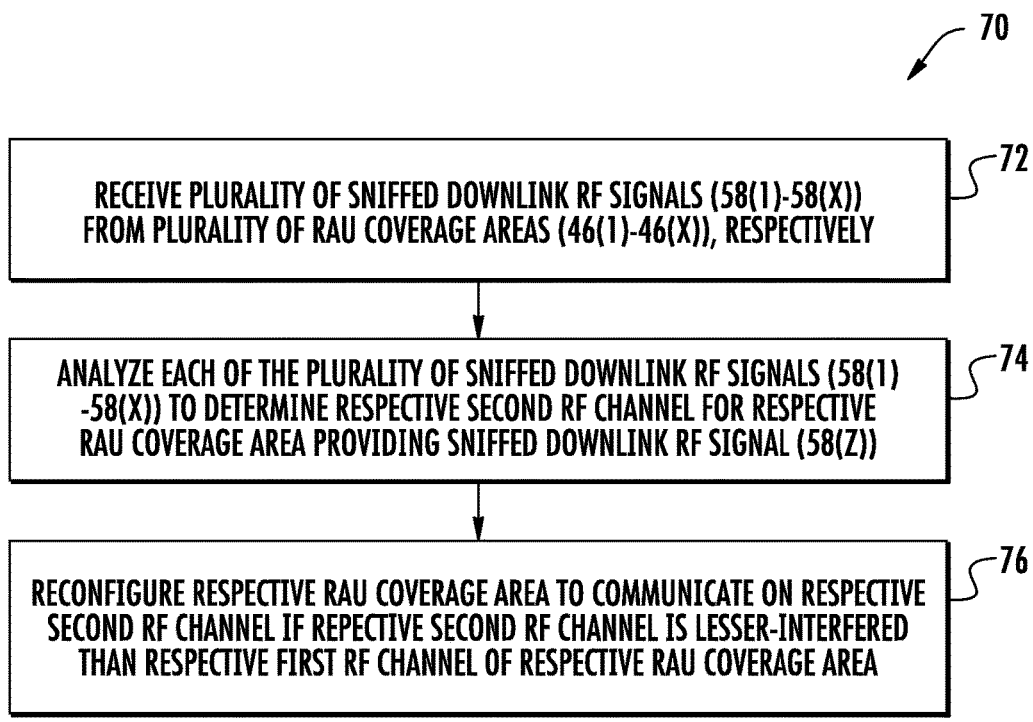
FIG. 4 is a flowchart illustrating an exemplary spectrum optimization process that can be performed by the spectrum optimization unit of FIG. 3 for detecting and reducing the adjacent-channel and the co-channel RF interferences in the DAS.

FIG. 4 is a flowchart illustrating an exemplary spectrum optimization process 70 that can be performed by the spectrum optimization unit 44 of FIG. 3 for detecting and reducing the adjacent-channel and the co-channel RF interferences in the DAS 40. As shown in FIG. 4, the spectrum optimization unit 44 receives the plurality of sniffed RF signals 58(1)-58(X) from the plurality of RAU coverage areas 46(1)-46(X), respectively (block 72). Each of the plurality of RAU coverage areas 46(1)-46(X) is configured to communicate on a respective first RF channel that is determined by a downlink communications signal among the one or more downlink communications signals 52(1)-52(Y). The spectrum optimization unit 44 is configured to analyze each of the plurality of sniffed RF signals 58(1)-58(X) to determine a respective second RF channel for a respective RAU coverage area providing the sniffed RF signal 58(Z) (block 74). If the respective second RF channel is lesser-interfered than the respective first RF channel of the respective RAU coverage area, the spectrum optimization unit 44 reconfigures the respective RAU coverage area to communicate on the respective second RF channel (block 76).

Figure 5:
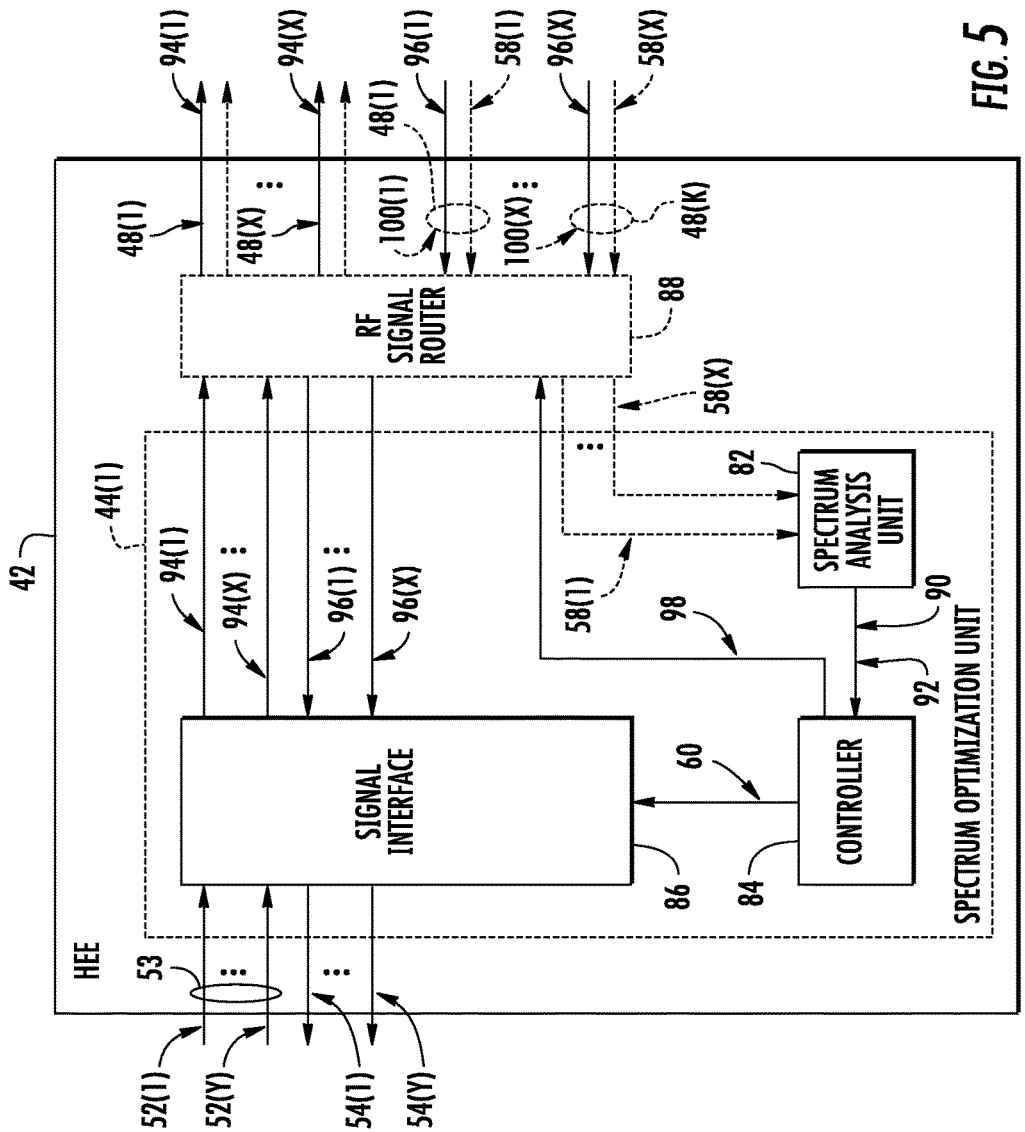
FIG. 5 is a schematic diagram of an exemplary spectrum optimization unit configured to detect and reduce the adjacent-channel and the co-channel RF interferences in the DAS of FIG. 3 using a spectrum analysis unit, a controller, and a signal interface.

In a non-limiting example, the spectrum optimization unit 44 may be provided as a combination of circuitries and/or functional blocks. To illustrate one exemplary embodiment of the spectrum optimization unit 44, FIG. 5 is provided. In this regard, FIG. 5 is a schematic diagram of an exemplary spectrum optimization unit 44(1) configured to detect and reduce the adjacent-channel and the co-channel RF interferences in the DAS 40 of FIG. 3 using a spectrum analysis unit 82, a controller 84, and a signal interface 86. Common elements between FIGS. 3 and 5 are shown therein with common element numbers and will not be re-described herein.

With reference to FIG. 5, the spectrum analysis unit 82 receives the plurality of sniffed RF signals 58(1)-58(X) from the plurality of RAU coverage areas 46(1)-46(X) (not shown), respectively. In a non-limiting example, the spectrum analysis unit 82 may receive the plurality of sniffed RF signals 58(1)-58(X) either directly from the plurality of RAU coverage areas 46(1)-46(X) or through an RF signal router 88 coupled to the plurality of communications mediums 48(1)-48(X). Each of the plurality of RAU coverage areas 46(1)-46(X) is configured to communicate on the respective first RF channel. The spectrum analysis unit 82 is configured to analyze each of the plurality of sniffed RF signals 58(1)-58(X) to determine whether there exists the respective second RF channel (not shown) in the RF channel set 53 that is lesser-interfered than the respective first RF channel of the respective RAU coverage area from which the sniffed RF signal is received. For some of the plurality of RAU coverage areas 46(1)-46(X), the respective second RF channels may be different from the respective first RF channels, indicating that the respective second RF channels are lesser-interfered than the respective first RF channels. In this regard, one or more second RF channels may be determined for the one or more RAU coverage areas among the plurality of RAU coverage areas 46(1)-46(X), respectively. In a non-limiting example, the spectrum analysis unit 82 then provides a spectrum analysis signal 90 to the controller 84. The spectrum analysis signal 90 comprises the one or more second RF channels for the one or more RAU coverage areas among the plurality of RAU coverage areas 46(1)-46(X).

With continuing reference to FIG. 5, in another non-limiting example, the controller 84 generates and provides the channel control signal 60 to the signal interface 86 in response to receiving the spectrum analysis signal 90. The signal interface 86 then reconfigures the one or more RAU coverage areas among the plurality of RAU coverage areas 46(1)-46(X) to communicate on the one or more second RF channels, respectively.

With continuing reference to FIG. 5, the spectrum analysis unit 82 also analyzes the plurality of sniffed RF signals 58(1)-58(X) to detect the power-leaking RAU in a RAU coverage area among the plurality of RAU coverage areas 46(1)-46(X) that interferes with another RAU coverage area among the plurality of RAU coverage areas 46(1)-46(X). If the power-leaking RAU is detected, the controller 84 can reduce the RF power level of the power-leaking RAU, thus reducing the adjacent-channel or the co-channel interference caused by the power-leaking RAU. In a non-limiting example, the spectrum analysis unit 82 may notify the controller 84 about the power-leaking RAU via a power leakage signal 92.

Furthermore, by analyzing the plurality of sniffed RF signals 58(1)-58(X), the spectrum analysis unit 82 is also able to determine whether the RAU coverage area among the plurality of RAU coverage areas 46(1)-46(X) is an over-sized RAU coverage area, such as the over-sized RAU coverage area 10'(2) of FIG. 2B. Accordingly, the controller 84 can reduce the RF power levels of the over-sized RAU coverage area to reduce the coverage boundary of the over-sized RAU coverage area. Furthermore, it is also possible to determine whether the RAU coverage area among the plurality of RAU coverage areas 46(1)-46(X) is an under-sized RAU coverage area. Accordingly, the controller 84 can increase the RF power levels of the under-sized RAU coverage area to increase the coverage boundary of the under-sized RAU coverage area.

With continuing reference to FIG. 5, the signal interface 86 also receives the one or more downlink communications signals 52(1)-52(Y). In a non-limiting example, the signal interface 86 may be configured to adapt the one or more downlink communications signals 52(1)-52(Y) into a plurality of downlink RF signals 94(1)-94(X) appropriate for communicating in the DAS 40 (not shown) of FIG. 3. In turn, the signal interface 86 provides the plurality of downlink RF signals 94(1)-94(X) to the RF signal router 88 for communicating to the plurality of RAU coverage areas 46(1)-46(X).

With continuing reference to FIG. 5, the RF signal router 88 is coupled to the plurality of RAU coverage areas 46(1)-46(X) over the plurality of communications mediums 48(1)-48(X), respectively. The RF signal router 88 provides the plurality of downlink RF signals 94(1)-94(X) to the plurality of RAU coverage areas 46(1)-46(X) over the respective downlink data signal paths 50DD (not shown) in the plurality of communications mediums 48(1)-48(X).

With continuing reference to FIG. 5, the RF signal router 88 receives a plurality of uplink RF signals 96(1)-96(X) from the plurality of RAU coverage areas 46(1)-46(X) over the respective uplink data signal paths 50UD (not shown) in the plurality of communications mediums 48(1)-48(X). The RF signal router 88 then provides the plurality of uplink RF signals 96(1)-96(X) to the signal interface 86. In a non-limiting example, the signal interface 86 adapts the plurality of uplink RF signals 96(1)-96(X) into the one or more uplink communications signals 54(1)-54(Y) that are appropriate to be provided to the one or more communications signals sources (not shown). The RF signal router 88 also receives the plurality of sniffed RF signals 58(1)-58(X) from the plurality of RAU coverage areas 46(1)-46(X) over the plurality of communications mediums 48(1)-48(X), respectively. The RF signal router 88 is configured to provide the plurality of sniffed RF signals 58(1)-58(X) to the spectrum analysis unit 82. In a non-limiting example, the RF signal router 88 may provide the plurality of sniffed RF signals 58(1)-58(X) to the spectrum analysis unit 82 in response to receiving a control signal 98 from the controller 84. In another non-limiting example, the RF signal router 88 may be configured receive a plurality of combined uplink signals 100(1)-100(X) from the plurality of RAU coverage areas 46(1)-46(X) over the respective uplink data signal paths 50UD in the plurality of communications mediums 48(1)-48(X). In this regard, the RF signal router 88 is configured to separate the plurality of uplink RF signals 96(1)-96(X) and the plurality of sniffed RF signals 58(1)-58(X) from the plurality of combined uplink signals 100(1)-100(X) before providing the plurality of uplink RF signals 96(1)-96(X) and the plurality of sniffed RF signals 58(1)-58(X) to the signal interface 86 and the spectrum analysis unit 82, respectively.

Figure 6:
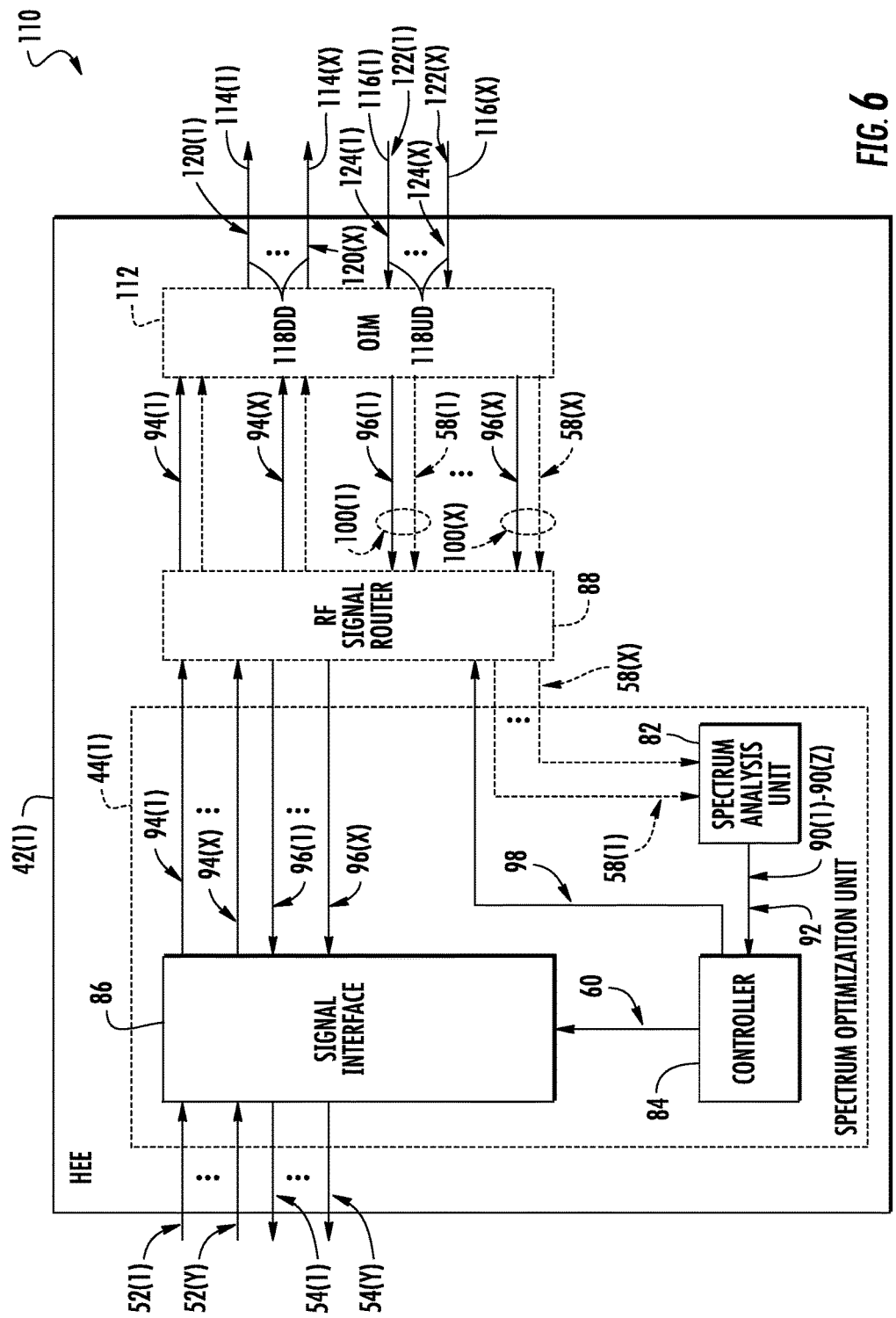
FIG. 6 is a schematic diagram of an exemplary HEE for a DAS comprising the spectrum optimization unit of FIG. 5 and configured to detect and reduce the adjacent-channel and the co-channel RF interferences in an optical fiber-based DAS.

As illustrated in FIG. 3, the plurality of communications mediums 48(1)-48(X) may be provided as the plurality of optical fiber-based communications mediums 48'(1)-48'(X). In this regard, FIG. 6 is a schematic diagram of an exemplary HEE 42(1) comprising the spectrum optimization unit 44(1) of FIG. 5 and configured to detect and reduce the adjacent-channel and the co-channel RF interferences in an optical fiber-based DAS 110. Common elements between FIGS. 5 and 6 are shown therein with common element numbers and will not be re-described herein.

With reference to FIG. 6, the HEE 42(1) comprises at least one optical interface module (OIM) 112. The OIM 112 is coupled to the plurality of RAU coverage areas 46(1)-46(X) (not shown) over a plurality of downlink optical fiber-based communications mediums 114(1)-114(X) and a plurality of uplink optical fiber-based communications mediums 116(1)-116(X), respectively. Each of the plurality of downlink optical fiber-based communications mediums 114(1)-114(X) comprises a respective downlink data signal path 118DD. Each of the plurality of downlink optical fiber-based communications mediums 114(1)-114(X) also comprises a respective uplink data signal path 118UD.

With continuing reference to FIG. 6, the OIM 112 receives and converts the plurality of downlink RF signals 94(1)-94(X) into a plurality of downlink optical signals 120(1)-120(X) for communicating to the plurality of RAU coverage areas 46(1)-46(X), respectively. The OIM 112 receives a plurality of uplink optical signals 122(1)-122(X) and a plurality of optical sniffed RF signals 124(1)-124(X) from the plurality of RAU coverage areas 46(1)-46(X), respectively. The OIM 112 converts the plurality of uplink optical signals 122(1)-122(X) into the plurality of uplink RF signals 96(1)-96(X), respectively, and provides the plurality of uplink RF signals 96(1)-96(X) to the RF signal router 88. The OIM 112 converts the plurality of optical sniffed RF signals 124(1)-124(X) into the plurality of sniffed RF signals 58(1)-58(X), respectively, and provides the plurality of sniffed RF signals 58(1)-58(X) to the RF signal router 88.

Figure 7:
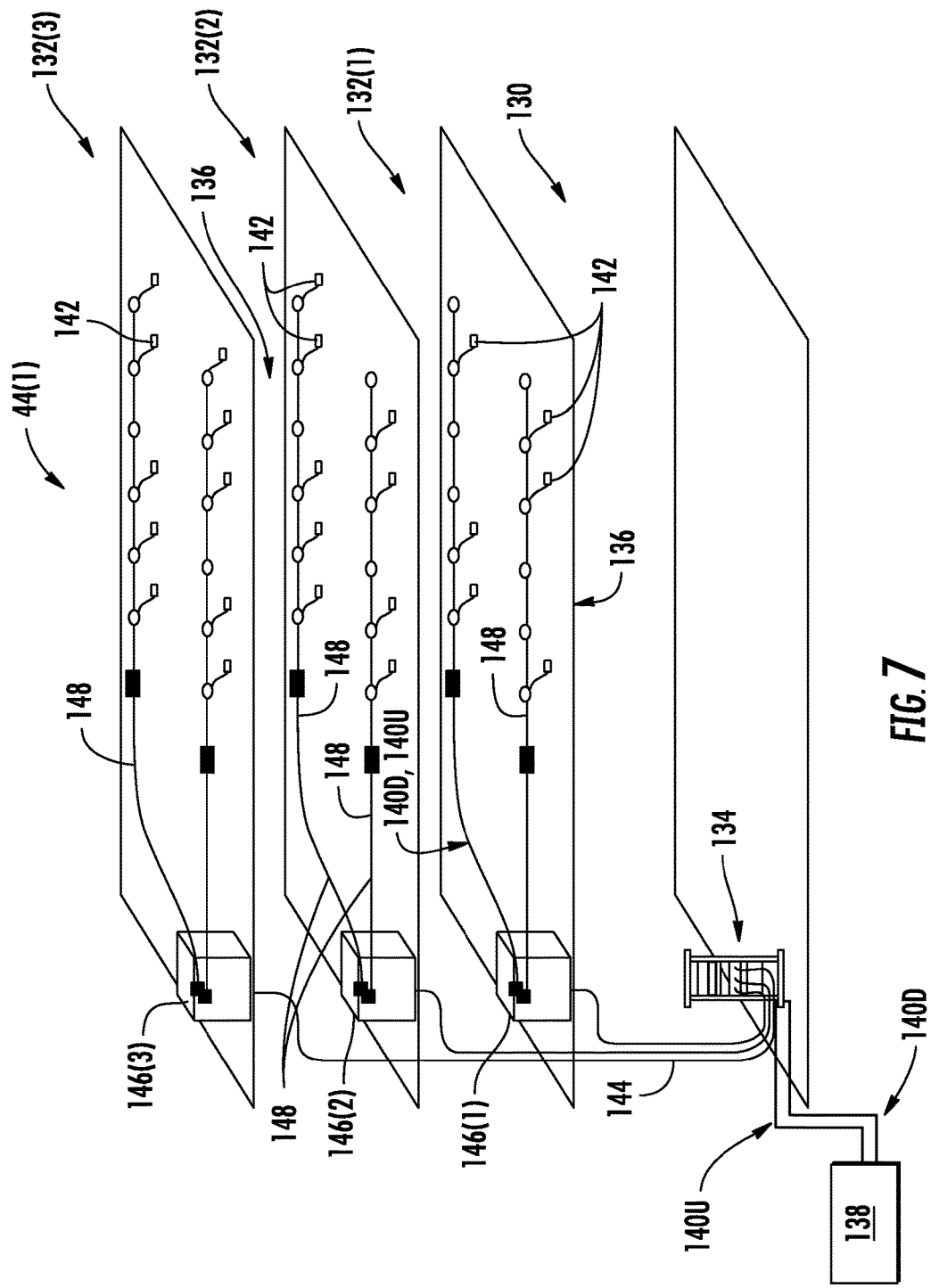
FIG. 7 is a partial schematic cut-away diagram of an exemplary building infrastructure in which an interference signal offset circuit, including the spectrum optimization unit of FIGS. 5 and 6, can be employed.

The spectrum optimization unit 44(1) of FIGS. 5 and 6 may be provided in an indoor environment, as illustrated in FIG. 7. FIG. 7 is a partial schematic cut-away diagram of an exemplary building infrastructure 130 in which the spectrum optimization unit 44(1) of FIGS. 5 and 6 can be employed. The building infrastructure 130 in this embodiment includes a first (ground) floor 132(1), a second floor 132(2), and a third floor 132(3). The floors 132(1)-132(3) are serviced by a central unit 134 to provide antenna coverage areas 136 in the building infrastructure 130. The central unit 134 is communicatively coupled to a base station 138 to receive downlink communications signals 140D from the base station 138. The central unit 134 receives uplink communications signals 140U from RAUs 142. The downlink communications signals 140D and uplink communications signals 140U communicated between the central unit 134 and the RAUs 142 are carried over a riser cable 144. The riser cable 144 may be routed through interconnect units (ICUs) 146(1)-146(3) dedicated to each of the floors 132(1)-132(3) that route the downlink communications signals 140D and uplink communications signals 140U to the RAUs 142 and also provide power to the RAUs 142 via array cables 148.

Figure 8:
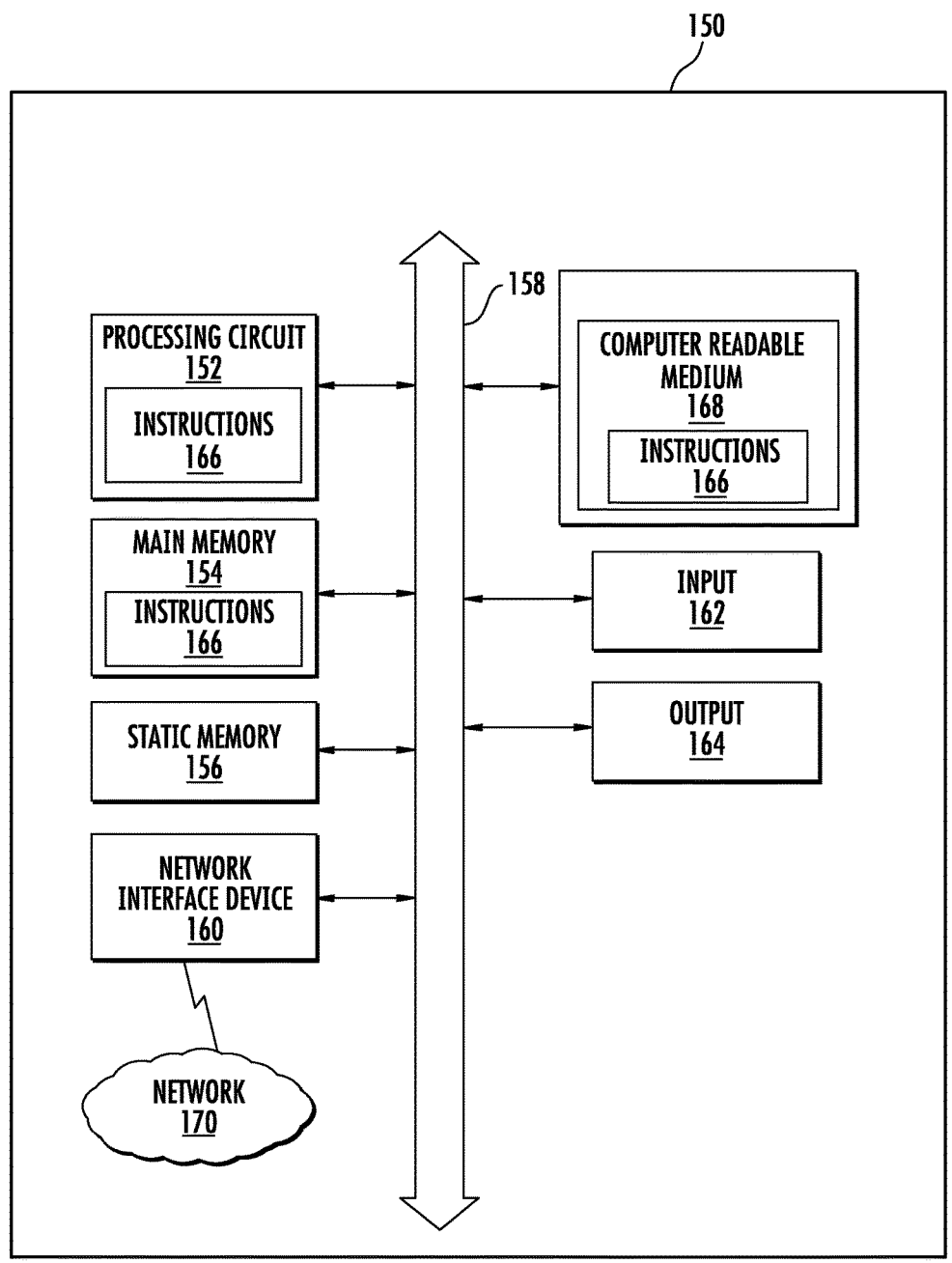
FIG. 8 is a schematic diagram of a generalized representation of an exemplary controller that can be included in the spectrum optimization unit of FIGS. 5 and 6 for detecting and reducing the adjacent-channel and the co-channel RF interferences in the DAS of FIG. 3, wherein an exemplary computer system is adapted to execute instructions from an exemplary computer-readable medium.

FIG. 8 is a schematic diagram illustrating additional details of an exemplary computer system 150 that could be employed in the controllers discussed above, including, but not limited to, the controller 84 in the spectrum optimization unit 44(1) of FIGS. 5 and 6. As discussed above, the controller 84 is configured to detect and reduce the adjacent-channel and the co-channel RF interferences in the DAS 40 of FIG. 3. In this regard, the computer system 150 is adapted to execute instructions from an exemplary computer-readable medium to perform these and/or any of the functions or processing described herein.

With reference to FIG. 8, the computer system 150 may include a set of instructions that may be executed to predict frequency interference to avoid or reduce interference in a multi-frequency DAS. The computer system 150 may be connected (e.g., networked) to other machines in a LAN, an intranet, an extranet, or the Internet. While only a single device is illustrated, the term "device" shall also be taken to include any collection of devices that individually or jointly execute a set (or multiple sets) of instructions to perform any one or more of the methodologies discussed herein. The computer system 150 may be a circuit or circuits included in an electronic board card, such as a printed circuit board (PCB), a server, a personal computer, a desktop computer, a laptop computer, a personal digital assistant (PDA), a computing pad, a mobile device, or any other device, and may represent, for example, a server or a user's computer.

The computer system 150 in this embodiment includes a processing circuit ("processor 152"), a main memory 154 (e.g., read-only memory (ROM), flash memory, dynamic random access memory (DRAM), such as synchronous DRAM (SDRAM), etc.), and a static memory 156 (e.g., flash memory, static random access memory (SRAM), etc.), which may communicate with each other via a data bus 158. Alternatively, the processor 152 may be connected to the main memory 154 and/or the static memory 156 directly or via some other connectivity bus or connection. The processor 152 may be a controller like the controller 84 of FIGS. 5 and 6. The main memory 154 and the static memory 156 may be any type of memory.

The processor 152 may be a microprocessor, central processing unit, or the like. More particularly, the processor 152 may be a complex instruction set computing (CISC) microprocessor, a reduced instruction set computing (RISC) microprocessor, a very long instruction word (VLIW) microprocessor, a processor implementing other instruction sets, or other processors implementing a combination of instruction sets. The processor 152 is configured to execute processing logic in instructions for performing the operations and steps discussed herein.

The computer system 150 may further include a network interface device 160. The computer system 150 also may or may not include an input 162, configured to receive input and selections to be communicated to the computer system 150 when executing instructions. The computer system 150 also may or may not include an output 164, including, but not limited to, a display, a video display unit (e.g., a liquid crystal display (LCD) or a cathode ray tube (CRT)), an alphanumeric input device (e.g., a keyboard), and/or a cursor control device (e.g., a mouse).

The computer system 150 may or may not include a data storage device that includes instructions 166 stored in a computer-readable medium 168. The instructions 166 may also reside, completely or at least partially, within the main memory 154 and/or within the processor 152 during execution thereof by the computer system 150, the main memory 154 and the processor 152 also constituting the computer-readable medium 168. The instructions 166 may further be transmitted or received over a network 170 via the network interface device 160.

While the computer-readable medium 168 is shown in an exemplary embodiment to be a single medium, the term "computer-readable medium" should be taken to include a single medium or multiple mediums (e.g., a centralized or distributed database, and/or associated caches and servers) that store the one or more sets of instructions. The term "computer-readable medium" shall also be taken to include any medium that is capable of storing, encoding, or carrying a set of instructions for execution by the processing device and that cause the processing device to perform any one or more of the methodologies of the embodiments disclosed herein. The term "computer-readable medium" shall accordingly be taken to include, but not be limited to, solid-state memories, optical mediums, and magnetic mediums.

The embodiments disclosed herein include various steps. The steps of the embodiments disclosed herein may be formed by hardware components or may be embodied in machine-executable instructions, which may be used to cause a general-purpose or special-purpose processor programmed with the instructions to perform the steps. Alternatively, the steps may be performed by a combination of hardware and software.

The embodiments disclosed herein may be provided as a computer program product, or software, that may include a machine-readable medium (or computer-readable medium) having stored thereon instructions, which may be used to program a computer system (or other electronic devices) to perform a process according to the embodiments disclosed herein. A machine-readable medium includes any mechanism for storing or transmitting information in a form readable by a machine (e.g., a computer). For example, a machine-readable medium includes: a machine-readable storage medium (e.g., ROM, random access memory ("RAM"), a magnetic disk storage medium, an optical storage medium, flash memory devices, etc.), and the like.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred.

It will be apparent to those skilled in the art that various modifications and variations can be made without departing from the spirit or scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

What is claimed is:

1. A spectrum optimization unit in a distributed antenna system (DAS), comprising:
a spectrum analysis unit communicatively coupled to a plurality of remote antenna unit (RAU) coverage areas in a DAS, the plurality of RAU coverage areas each configured to communicate on a respective first radio frequency (RF) channel;
the spectrum analysis unit configured to:
receive a plurality of sniffed RF signals from the plurality of RAU coverage areas, respectively, wherein each of the plurality of sniffed RF signals comprises one or more RF signals sniffed by at least one RAU in a respective RAU coverage area; and
for each of the plurality of sniffed RF signals:
analyze the one or more RF signals comprised in the plurality of sniffed RF signals; and
determine a respective second RF channel for the respective RAU coverage area if the respective second RF channel is lesser-interfered than the respective first RF channel; and
a controller configured to reconfigure one or more RAU coverage areas among the plurality of RAU coverage areas to communicate on one or more respective second RF channels in response to the one or more respective second RF channels being determined by the spectrum analysis unit, wherein:
  each of the plurality of sniffed RF signals comprises one or more downlink RF signals sniffed by the at least one RAU on the respective first RF channel in the respective RAU coverage area;
  the spectrum analysis unit is further configured to identify a power-leaking RAU in an RAU coverage area among the plurality of RAU coverage areas, wherein the power-leaking RAU interferes with another RAU coverage area among the plurality of RAU coverage areas that is different from the respective RAU coverage area of the power-leaking RAU; and
  the controller is further configured to reduce RF power level of the power-leaking RAU identified by the spectrum analysis unit.

2. The spectrum optimization unit of claim 1, wherein each of the plurality of sniffed RF signals comprises one or more uplink RF signals sniffed by the at least one RAU on the respective first RF channel in the respective RAU coverage area.

3. The spectrum optimization unit of claim 1, wherein each of the plurality of sniffed RF signals comprises one or more configured RF signals sniffed by the at least one RAU on the respective first RF channel in the respective RAU coverage area.

4. The spectrum optimization unit of claim 1, wherein each of the plurality of sniffed RF signals comprises one or more ad hoc RF signals sniffed by the at least one RAU on the respective first RF channel in the respective RAU coverage area.

5. The spectrum optimization unit of claim 1, wherein the spectrum analysis unit is further configured to analyze the one or more RF signals comprised in each of the plurality of sniffed RF signals to determine a downlink RF signal among the one or more RF signals that is received from a cellular base station (BS).

6. The spectrum optimization unit of claim 1, wherein the spectrum analysis unit is further configured to analyze the one or more RF signals comprised in each of the plurality of sniffed RF signals to determine a downlink RF signal among the one or more RF signals that is received from a mobile station (MS).

7. A spectrum optimization unit in a distributed antenna system (DAS), comprising:
  a spectrum analysis unit communicatively coupled to a plurality of remote antenna unit (RAU) coverage areas in a DAS, the plurality of RAU coverage areas each configured to communicate on a respective first radio frequency (RF) channel;
  the spectrum analysis unit configured to:
    receive a plurality of sniffed RF signals from the plurality of RAU coverage areas, respectively, wherein each of the plurality of sniffed RF signals comprises one or more RF signals sniffed by at least one RAU in a respective RAU coverage area; and
    for each of the plurality of sniffed RF signals:
      analyze the one or more RF signals comprised in the plurality of sniffed RF signals; and
      determine a respective second RF channel for the respective RAU coverage area if the respective second RF channel is lesser-interfered than the respective first RF channel; and
  a controller configured to reconfigure one or more RAU coverage areas among the plurality of RAU coverage areas to communicate on one or more respective second RF channels in response to the one or more respective second RF channels being determined by the spectrum analysis unit
  a signal interface configured to:
    receive one or more downlink communications signals from one or more communications signal sources, each of the one or more downlink communications signals is associated with a respective RF channel;
    receive a channel control signal from the controller, wherein the channel control signal identifies the one or more RAU coverage areas to be reconfigured to operate on the one or more respective second RF channels; and
    for each of the one or more RAU coverage areas to be reconfigured to operate on the one or more respective second RF channels:
      identify a downlink communications signal among the one or more downlink communications signals received from the one or more communications signal sources, wherein the downlink communications signal is associated with a respective RF channel that matches the respective second RF channel determined by the spectrum analysis unit for the respective RAU coverage area; and
      route the identified downlink communications signal for distribution to the respective RAU coverage area.

8. A spectrum optimization unit in a distributed antenna system (DAS), comprising:
  a spectrum analysis unit communicatively coupled to a plurality of remote antenna unit (RAU) coverage areas in a DAS, the plurality of RAU coverage areas each configured to communicate on a respective first radio frequency (RF) channel;
  the spectrum analysis unit configured to:
    receive a plurality of sniffed RF signals from the plurality of RAU coverage areas, respectively, wherein each of the plurality of sniffed RF signals comprises one or more RF signals sniffed by at least one RAU in a respective RAU coverage area; and
    for each of the plurality of sniffed RF signals:
      analyze the one or more RF signals comprised in the plurality of sniffed RF signals; and
      determine a respective second RF channel for the respective RAU coverage area if the respective second RF channel is lesser-interfered than the respective first RF channel; and
  a controller configured to reconfigure one or more RAU coverage areas among the plurality of RAU coverage areas to communicate on one or more respective second RF channels in response to the one or more respective second RF channels being determined by the spectrum analysis unit, wherein:
  each of the plurality of sniffed RF signals comprises one or more downlink RF signals sniffed by the at least one RAU on the respective first RF channel in the respective RAU coverage area; and
  the spectrum analysis unit is further configured to:
    identify an RAU coverage area among the plurality of RAU coverage areas as an over-sized RAU coverage area if the RAU coverage area has an expanded coverage boundary larger than a planned coverage boundary; and identify an RAU coverage area among the plurality of RAU coverage areas as an under-sized RAU coverage area if the RAU coverage area has a reduced coverage boundary smaller than the planned coverage boundary; and the controller is further configured to reduce the expanded coverage boundary of the over-sized RAU coverage area by reducing RF power level of one or more RAUs in the over-sized RAU coverage area.

9. A spectrum optimization unit in a distributed antenna system (DAS), comprising:
a spectrum analysis unit communicatively coupled to a plurality of remote antenna unit (RAU) coverage areas in a DAS, the plurality of RAU coverage areas each configured to communicate on a respective first radio frequency (RF) channel;
the spectrum analysis unit configured to:
receive a plurality of sniffed RF signals from the plurality of RAU coverage areas, respectively, wherein each of the plurality of sniffed RF signals comprises one or more RF signals sniffed by at least one RAU in a respective RAU coverage area; and
for each of the plurality of sniffed RF signals:
analyze the one or more RF signals comprised in the plurality of sniffed RF signals; and
determine a respective second RF channel for the respective RAU coverage area if the respective second RF channel is lesser-interfered than the respective first RF channel; and
a controller configured to reconfigure one or more RAU coverage areas among the plurality of RAU coverage areas to communicate on one or more respective second RF channels in response to the one or more respective second RF channels being determined by the spectrum analysis unit, wherein:
each of the plurality of sniffed RF signals comprises one or more downlink RF signals sniffed by the at least one RAU on the respective first RF channel in the respective RAU coverage area; and
the spectrum analysis unit is further configured to:
identify an RAU coverage area among the plurality of RAU coverage areas as an over-sized RAU coverage area if the RAU coverage area has an expanded coverage boundary larger than a planned coverage boundary; and
identify an RAU coverage area among the plurality of RAU coverage areas as an under-sized RAU coverage area if the RAU coverage area has a reduced coverage boundary smaller than the planned coverage boundary; and
the controller is further configured to increase the reduced coverage boundary of the under-sized RAU coverage area by increasing RF power level of one or more RAUs in the under-sized RAU coverage area.

10. A method for reducing radio frequency (RF) interferences in a plurality of remote antenna unit (RAU) coverage areas in a distributed antenna system (DAS), comprising:
receiving a plurality of sniffed RF signals from a plurality of RAU coverage areas, respectively, wherein each of the plurality of RAU coverage areas is configured to communicate on a respective first RF channel;
for each of the plurality of sniffed RF signals received from the plurality of RAU coverage areas:
analyzing the plurality of sniffed RF signals to determine a respective second RF channel for a respective RAU coverage area if the respective second RF channel is lesser-interfered than the respective first RF channel of the respective RAU coverage area; and
reconfiguring the respective RAU coverage area to communicate on the respective second RF channel;
identifying a power-leaking RAU in an RAU coverage area among the plurality of RAU coverage areas, wherein the power-leaking RAU interferes with another RAU coverage area among the plurality of RAU coverage areas that is different from the respective RAU coverage area of the power-leaking RAU;
reducing RF power level of the power-leaking RAU;
identifying an RAU coverage area among the plurality of RAU coverage areas as an over-sized RAU coverage area if the RAU coverage area has an expanded coverage boundary larger than a planned coverage boundary;
identifying an RAU coverage area among the plurality of RAU coverage areas as an under-sized RAU coverage area if the RAU coverage area has a reduced coverage boundary smaller than the planned coverage boundary;
reducing the expanded coverage boundary of the over-sized RAU coverage area by reducing RF power level of one or more RAUs in the over-sized RAU coverage area; and
increasing the reduced coverage boundary of the under-sized RAU coverage area by increasing RF power level of one or more RAUs in the under-sized RAU coverage area.

11. A distributed antenna system (DAS), comprising:
a plurality of remote antenna unit (RAU) coverage areas in a DAS, wherein each of the plurality of RAU coverage areas is configured to communicate on a respective first radio frequency (RF) channel; and
a head-end equipment (HEE) coupled to the plurality of RAU coverage areas over a plurality of communications mediums, respectively, the HEE comprising a spectrum optimization unit;
the spectrum optimization unit comprising:
a spectrum analysis unit configured to:
receive a plurality of sniffed RF signals from the plurality of RAU coverage areas, respectively, wherein each of the plurality of sniffed RF signals comprises one or more RF signals sniffed by at least one RAU in a respective RAU coverage area; and
for each of the plurality of sniffed RF signals:
analyze the one or more RF signals comprised in the plurality of sniffed RF signals; and
determine a respective second RF channel for the respective RAU coverage area if the respective second RF channel is lesser-interfered than the respective first RF channel; and
a controller configured to reconfigure one or more RAU coverage areas among the plurality of RAU coverage areas to communicate on one or more respective second RF channels in response to the one or more respective second RF channels being determined by the spectrum analysis unit, wherein the spectrum optimization unit further comprises a signal interface configured to:
receive one or more downlink communications signals from one or more communications signal sources, each of the one or more downlink communications signals associated with a respective RF channel;
receive a control signal from the controller, wherein the control signal identifies the one or more RAU coverage areas to be reconfigured to operate on the one or more respective second RF channels; and for each of the one or more RAU coverage areas to be reconfigured to operate on the one or more respective second RF channels:
identify a downlink communications signal among the one or more downlink communications signals received from the one or more communications signal sources, wherein a respective RF channel of the downlink communications signal is the same as the respective second RF channel of the respective RAU coverage area; and
route the identified downlink communications signal to the respective RAU coverage area.

12. The DAS of claim 11, wherein each of the plurality of communications mediums comprises:
a respective downlink data signal path for communicating the one or more downlink communications signals to the plurality of RAU coverage areas; and
a respective uplink data signal path for receiving one or more uplink communications signals from the plurality of RAU coverage areas.

13. The DAS of claim 12, wherein the RF signal router configured to:
receive the one or more downlink communications signals from the signal interface; and
provide the one or more downlink communications signals to the plurality of RAU coverage areas over the respective downlink data signal path in the plurality of communications mediums.

14. The DAS of claim 13, wherein the RF signal router is further configured to:
receive the one or more uplink communications signals and the plurality of sniffed RF signals from the plurality of RAU coverage areas over the respective uplink data signal path in the plurality of communications mediums;
provide the plurality of sniffed RF signals to the spectrum analysis unit; and
provide the one or more uplink communications signals to the signal interface.

15. The DAS of claim 12, wherein:
the spectrum analysis unit is further configured to identify a power-leaking RAU in an RAU coverage area among the plurality of RAU coverage areas, wherein the power-leaking RAU interferes with another RAU coverage area among the plurality of RAU coverage areas that is different from the respective RAU coverage area of the power-leaking RAU; and
the controller is further configured to reduce RF power level of the power-leaking RAU identified by the spectrum analysis unit.

16. The DAS of claim 11, wherein the plurality of communications mediums is a plurality of optical fiber-based communications mediums, each of the plurality of optical fiber-based communications mediums comprising:
a respective downlink data signal path for communicating the one or more downlink communications signals to the plurality of RAU coverage areas; and
a respective uplink data signal path for receiving one or more uplink communications signals from the plurality of RAU coverage areas.

17. The DAS of claim 16, wherein:
the respective downlink data signal path is provided by a respective downlink data optical fiber; and
the respective uplink data signal path is provided by a respective uplink data optical fiber.

18. The DAS of claim 16, wherein the HEE further comprises an RF signal router configured to:
receive the one or more downlink communications signals from the signal interface;
provide the one or more downlink communications signals to at least one optical interface module (OIM) in the HEE;
receive the plurality of sniffed RF signals from the at least one OIM;
provide the plurality of sniffed RF signals to the spectrum analysis unit;
receive the one or more uplink communications signals from the at least one OIM; and
provide the one or more uplink communications signals to the signal interface.

19. The DAS of claim 18, wherein the at least one OIM is configured to:
convert the one or more downlink communications signals into a plurality of downlink optical signals; and
provide the plurality of downlink optical signals to the plurality of RAU coverage areas over the respective downlink data signal path in the plurality of optical fiber-based communications mediums.

20. The DAS of claim 18, wherein the at least one OIM is configured to:
receive a plurality of optical sniffed RF signals from the plurality of RAU coverage areas over the respective uplink data signal path in the plurality of optical fiber-based communications mediums, respectively;
convert the plurality of optical sniffed RF signals into the plurality of sniffed RF signals, respectively;
provide the plurality of sniffed RF signals to the spectrum analysis unit;
receive a plurality of uplink optical signals from the plurality of RAU coverage areas over the respective uplink data signal path in the plurality of optical fiber-based communications mediums;
convert the plurality of uplink optical signals into the one or more uplink communications signals; and
provide the one or more uplink communications signals to the signal interface.

21. A distributed antenna system (DAS), comprising:
a plurality of remote antenna unit (RAU) coverage areas in a DAS, wherein each of the plurality of RAU coverage areas is configured to communicate on a respective first radio frequency (RF) channel; and
a head-end equipment (HEE) coupled to the plurality of RAU coverage areas over a plurality of communications mediums, respectively, the HEE comprising a spectrum optimization unit;
the spectrum optimization unit comprising:
a spectrum analysis unit configured to:
receive a plurality of sniffed RF signals from the plurality of RAU coverage areas, respectively, wherein each of the plurality of sniffed RF signals comprises one or more RF signals sniffed by at least one RAU in a respective RAU coverage area; and
for each of the plurality of sniffed RF signals:
analyze the one or more RF signals comprised in the plurality of sniffed RF signals; and
determine a respective second RF channel for the respective RAU coverage area if the respective second RF channel is lesser-interfered than the respective first RF channel; and
a controller configured to reconfigure one or more RAU coverage areas among the plurality of RAU coverage areas to communicate on one or more respective second RF channels in response to the one or more respective second RF channels being determined by the spectrum analysis unit, wherein:

the spectrum analysis unit is further configured to:
- identify an RAU coverage area among the plurality of RAU coverage areas as an over-sized RAU coverage area if the RAU coverage area has an expanded coverage boundary larger than a planned coverage boundary; and
- identify an RAU coverage area among the plurality of RAU coverage areas as an under-sized RAU coverage area if the RAU coverage area has a reduced coverage boundary smaller than the planned coverage boundary; and the controller is further configured to:
- reduce the expanded coverage boundary of the over-sized RAU coverage area by reducing RF power level of one or more RAUs in the over-sized RAU coverage area; and
- increase the reduced coverage boundary of the under-sized RAU coverage area by increasing RF power level of one or more RAUs in the under-sized RAU coverage area.

* * * * *

UNITED STATES PATENT AND TRADEMARK OFFICE
CERTIFICATE OF CORRECTION

PATENT NO. : 10,524,133 B2  
APPLICATION NO. : 15/807286  
DATED : December 31, 2019  
INVENTOR(S) : Dror Harel It is certified that error appears in the above-identified patent and that said Letters Patent is hereby corrected as shown below:

On the Title Page

In Column 1, item (71), Applicant, Line 1, delete "Corning Optical Communications Wireless Ltd, Airport City (Il)" and insert -- Coming Optical Communications LLC, Hickory, NC (US) --, therefor.

In Column 2, item (56), other publications, Line 1, delete "Iinternational" and insert -- International --, therefor.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*